United States Patent
Saito (10) Patent No.: US 10,278,577 B2
(45) Date of Patent: May 7, 2019

(54) FOCUSING SYSTEM AND METHOD

(71) Applicant: CANON KABUSHIKI KAISHA, Tokyo (JP)

(72) Inventor: Kenichi Saito, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 15/721,484

(22) Filed: Sep. 29, 2017

(65) Prior Publication Data

US 2018/0020914 A1 Jan. 25, 2018

Related U.S. Application Data

(63) Continuation of application No. 14/632,971, filed on Feb. 26, 2015, now Pat. No. 9,775,514.

(51) Int. Cl.
| | |
|---|---|
| *A61B 3/10* | (2006.01) |
| *A61B 3/12* | (2006.01) |
| *A61B 3/00* | (2006.01) |
| *G02B 17/02* | (2006.01) |
| *G02B 26/06* | (2006.01) |
| *A61B 3/14* | (2006.01) |

(52) U.S. Cl.
CPC .............. *A61B 3/12* (2013.01); *A61B 3/0075* (2013.01); *A61B 3/1015* (2013.01); *A61B 3/1025* (2013.01); *A61B 3/14* (2013.01); *G02B 17/023* (2013.01); *G02B 26/06* (2013.01)

(58) Field of Classification Search
CPC ... A61B 3/0075; A61B 3/1015; A61B 3/1025; A61B 3/103; A61B 3/1035; A61B 3/12; G02B 17/023; G02B 26/06

USPC ................ 351/205, 210, 220, 221
See application file for complete search history.

(56) References Cited

U.S. PATENT DOCUMENTS

| | | | |
|---|---|---|---|
| 6,890,076 B2* | 5/2005 | Roorda | G01J 9/00 351/205 |
| 8,488,895 B2* | 7/2013 | Muller | G02B 21/0028 351/206 |
| 9,775,514 B2* | 10/2017 | Saito | A61B 3/12 |
| 2011/0096337 A1* | 4/2011 | Hirose | A61B 3/102 356/491 |

* cited by examiner

*Primary Examiner* — Nicholas R. Pasko
(74) *Attorney, Agent, or Firm* — Canon U.S.A., Inc. IP Division (57) ABSTRACT

An apparatus for measuring a fundus of a subject. The apparatus includes a focusing unit which adjusts a defocus of the apparatus. The focusing unit includes a first focusing mirror and a second focusing mirror. The first focusing mirror and second focusing mirror are arranged so that an incident beam from the light source entering the focusing unit and an emitted beam exiting the focusing unit are substantially parallel to each other. Adjustment of the defocus is accomplished by moving both first focusing mirror and second focusing mirror such that incident beam and emitted beam remain substantially parallel to each other. The apparatus includes a wavefront sensor for detecting a shape of a wavefront. The apparatus includes a wavefront correction device. The wavefront correction device adjusts a wavefront of the light from the light source based on the shape of the wavefront detected by the wavefront sensor.

19 Claims, 12 Drawing Sheets

FOCUSING SYSTEM AND METHOD

CROSS REFERENCE TO RELATED APPLICATION

This application is a continuation, and claims the benefit, of U.S. patent application Ser. No. 14/632,971 filed Feb. 26, 2015. U.S. patent application Ser. No. 14/632,971 is hereby incorporated by reference herein in its entirety.

BACKGROUND

Field of Art

The present disclosure relates to a system and method for adjusting the focus in an ophthalmoscope.

Description of the Related Art

In recent years, scanning light ophthalmoscopes (SLOs) that irradiate the fundus with laser light in two dimensions and receive reflected light therefrom and imaging apparatuses that utilize the interference of low coherence light have been developed as ophthalmic image pickup apparatuses. Thus, SLOs have become important tools for the study of the human retina in both normal and diseased eyes.

The resolution of such ophthalmic image pickup apparatuses has been improved by, for example, achieving high NA of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of acquired images.

One solution to this issue is an adaptive optics SLO (AO-SLO) in which the adaptive optics (AO) includes a correction optical system that measures the aberration of the eye and corrects the aberration. The AO-SLO or an adaptive optics optical coherence tomograph (AO-OCT) can measure the wavefront of the eye using a Shack-Hartmann wavefront sensor system. A deformable mirror or a spatial-phase modulator can then be driven to correct the measured wavefront, and an image of the fundus is acquired can then be acquired. This technique allows for the AO-SLO or the AO-OCT to obtain high resolution images of fundus despite the aberration introduced by intervening material such as the cornea and the lens of the eye.

SUMMARY

In one embodiment, an apparatus for measuring a fundus of a subject. The apparatus includes an input for receiving light from a light source. The apparatus includes a plurality of optically conjugate planes. The apparatus includes a focusing unit which adjusts a defocus of the apparatus. The focusing unit includes a first focusing mirror and a second focusing mirror. The first focusing mirror and the second focusing mirror are arranged so that an incident beam from the light source entering the focusing unit and an emitted beam exiting the focusing unit are substantially parallel to each other. Adjustment of the defocus is accomplished by moving both the first focusing mirror and the second focusing mirror such that the incident beam and the emitted beam remain substantially parallel to each other. The plurality of optically conjugate planes do not substantially move as the defocus is adjusted by moving both the first focusing mirror and the second focusing mirror. The apparatus includes a wavefront sensor for detecting a shape of a wavefront. The apparatus includes a wavefront correction device. The wavefront correction device adjusts a wavefront of the light from the light source based on the shape of the wavefront detected by the wavefront sensor.

In another embodiment, the apparatus may further comprise the light source.

In another embodiment, the first focusing mirror may be a concave mirror.

In another embodiment, the second focusing mirror may be a convex mirror.

In another embodiment, the relative position of the first focusing mirror to the second focusing mirror may remain unchanged during focusing.

In another embodiment, the wavefront sensor may detect aberrations after the focusing unit has corrected the defocus by moving the first focusing mirror and the second focusing mirror, and the wavefront correction device may correct aberrations based on the aberrations detected after the focusing unit has corrected the defocus.

In another embodiment, the wavefront sensor may detect the defocus generated by the subject, and the focusing unit may correct the defocus by moving the first focusing mirror and the second focusing mirror based on the defocus detected by the wavefront sensor.

In another embodiment, the wavefront correction device may correct aberrations while the focusing unit is correcting defocus.

In another embodiment, the wavefront correction device may start correcting aberrations after the focusing has started correcting defocus and the defocus is below a threshold, and the focusing unit continues to adjust defocus.

In another embodiment, the defocus may be generated by the subject.

In another embodiment, the incident beam and the emitted beam may remain parallel such that an optical axis of the incident beam and an optical axis of the emitted beam are parallel and are not collinear with each other.

In another embodiment, the focusing unit may not include an optical lens.

In another embodiment, the adjustment of the defocus may be accomplished by moving both the first focusing mirror and the second focusing mirror along a path that is substantially parallel to an optical axis of the incident beam and an optical axis of the emitted beam.

In another embodiment, the incident beam is not collimated when it strikes the first focusing mirror.

In another embodiment, the apparatus may further comprise a detector for detecting light from the subject which has been reflected by the focusing mirrors and has been corrected by the wavefront correction device.

In another embodiment, the apparatus may further comprise a scanner for scanning the light from light source across the subject. In another embodiment, the scanner may be positioned between the wavefront correction device and the focusing unit.

In another embodiment, the wavefront sensor may be positioned at a first conjugate plane among the plurality of optically conjugate planes, wherein all of the conjugate planes among the plurality of optically conjugate planes are substantially optically conjugate with each other. The wavefront correction device may be positioned at a second conjugate plane among the plurality of conjugate planes.

In another embodiment, the plurality of curved mirrors may be used to position the wavefront sensor at the first conjugate plane among the plurality of conjugate planes and the wavefront correction device at the second conjugate plane among the plurality of conjugate planes.

In another embodiment, the apparatus may further comprise a detector for detecting light from the subject is positioned at a fourth conjugate plane among the plurality of conjugate planes; a scanner for scanning the light from light source across the subject is positioned at a fifth conjugate plane among the plurality of conjugate planes.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following can be applied to an object to be inspected such as an eye to be inspected, skin, and internal organs.

Ophthalmoscope

Figure 1:
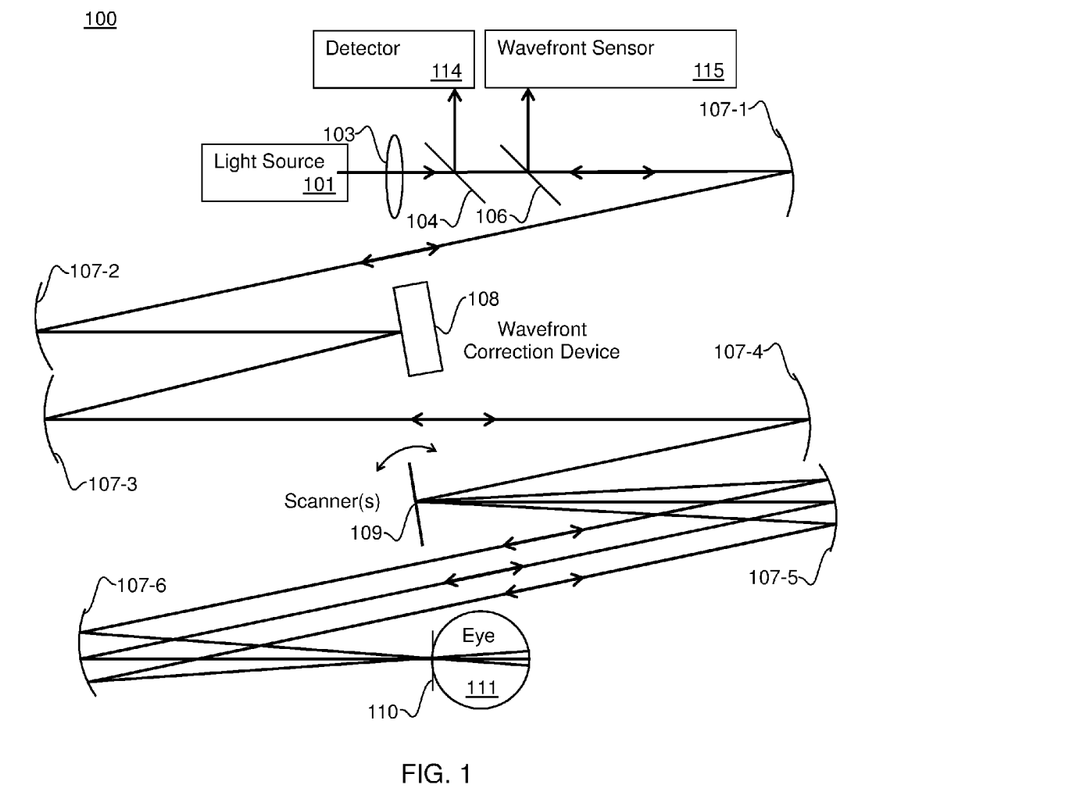
FIG. 1 is an illustration of an ophthalmoscope in which an embodiment may be implemented.

A first embodiment 100 is described with reference to a fundus image photographing apparatus such as the photographing apparatus illustrated in FIG. 1.

Embodiments are directed towards systems, methods, and software which are used in connection with an imaging system such as an ophthalmoscope. FIG. 1 is an illustration of an exemplary ophthalmoscope 100. An ophthalmoscope is a system or apparatus for obtaining information about an interior portion of the eye 111 (e.g., the fundus).

An exemplary embodiment may be a scanning ophthalmoscope. A scanning ophthalmoscope 100 scans a spot across the eye 111. The spot may be a spot of light from a light source 101 that is scanned across the eye 111.

In an exemplary embodiment, the spot of light is produced by a light source 101. The light source 101 may be incorporated into the ophthalmoscope 100; alternatively, the ophthalmoscope may include an input for receiving a light source 101. The input for the light source 101 may be a fiber optic input or a free space input. The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare for a person to be inspected and maintain imaging resolution.

In an exemplary embodiment, light emitted from the light source 101 is radiated as collimated light. The light from the light source may enter the ophthalmoscope via a single mode or multimode fiber optic cable and be collimated by a collimator 103. The collimator may be a grin lens 103 and/or may include one or more free space lenses.

In an exemplary embodiment, the polarization of the irradiated light may be adjusted by a polarization adjusting member provided in a path of the single-mode optical fiber. In an alternative configuration, the light source 101 is polarized and transmitted via polarization maintain fiber. In another configuration, the polarization adjusting member may be placed after a collimator 103. Alternatively, the polarization adjusting member may be replaced with a polarizer.

The light radiated from the collimator 103 passes through a first light division portion 104 including a beam splitter. An exemplary embodiment may include an adaptive optical system. Exemplary embodiments include both systems that do and do not include the adaptive optical system.

The adaptive optical system includes a light division portion 106, a wavefront sensor 115, wavefront correction device 108, and reflective mirrors 107-1 to 107-4 for guiding the measuring light to those components. The reflective mirrors 107-1 to 107-4 are provided to guide the measuring light to and from the pupil of an eye 111, the wavefront sensor 115, and the wavefront correction device 108. The wavefront sensor 115 and the wavefront correction device 108 may be in an optically conjugate relationship. A beam splitter may be used as the light division portion 106. The wavefront sensor 115 may be a Shack-Hartmann sensor.

The measuring light passing through the light division portion 106 is reflected off the reflective mirrors 107-1 and 107-2 to enter the wavefront correction device 108. The measuring light reflected off the wavefront correction device 108 and is further reflected off the reflective mirrors 107-3 and 107-4.

In one embodiment, the wavefront correction device 108 is a deformable mirror. In an alternative embodiment, one or two spatial phase modulators including a liquid crystal element is used as the wavefront correction device 108 which is not illustrated. The liquid crystal element may modulate a phase of only a specific polarized component. In which case, two liquid crystal elements may be employed to modulate substantially orthogonal polarized components of the measuring light.

The measuring light reflected off mirror 107-4 is two-dimensionally scanned by a scanning optical system 109 which may be part of a scanning unit. In an exemplary embodiment, the scanning optical system 109 includes a first scanner 109-1 and a second scanner 109-2. The first scanner 109-1 may be part of a first scanning unit. The second scanner 109-2 may be part of a second scanning unit. The first scanner 109-1 rotates around the first axis, while the second scanner 109-2 rotates around a second axis. The first axis is substantially orthogonal to the second axis. In one embodiment the first scanner 109-1 and the second scanner 109-2 may be incorporated into a single device that rotates along both axis. In an alternative embodiment, the first scanner 109-1 and the second scanner may be spatially separated from each other while being in an optically conjugate relationship with each other.

The first scanner 109-1 is rotating in the x-y plane, while the second scanner 109-2 is rotating in the z-x plane. In the context of the present application, rotating the measuring light in a first plane around the first axis is equivalent to rotating the measuring light 105 in the first plane and is equivalent to scanning the spot of light in the main scanning direction or the lateral direction of the object being imaged. In the context of the present application, rotating the measuring light in a second plane around the second axis is equivalent to rotating the measuring light 105 in the second plane and is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single scanning mirror that is rotated around the first axis by the first scanner 109-1 and around the second axis by the second scanner 109-2 that is substantially orthogonal to the first axis. An exemplary embodiment may also use non-mechanical beam steering techniques.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency.

The measuring light scanned by the scanning optical system 109 is radiated to the eye 111 via mirrors 107-5 and 107-6. The measuring light radiated to the eye 111 is reflected, scattered, or absorbed on the fundus.

Mirrors 107-1 through 107-6 may be spherical or other optical components such as lenses instead of mirrors. Although mirrors are typically used to avoid back reflection issues effecting the performance of the wavefront sensor 115

Reflected light which is produced by reflection or scattering on a retina of the eye 111 then travels in the reverse direction along the same path as in the case of incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, embodiments are not limited to a Shack-Hartmann sensor. Another wavefront measurement unit, for example, a curvature sensor may be employed or a method of obtaining the wavefront by reverse calculation from the formed spot images may also be employed.

When the reflected light passes through the light division portion 106, a part thereof is reflected on to the light division portion 104 and is guided to a light intensity sensor 114. The light intensity sensor 114 converts the light into an electrical signal.

Figure 2:
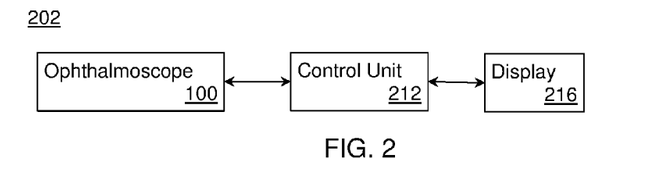
FIG. 2 is an illustration of a system in which an embodiment may be implemented.

FIG. 2 is an illustration of system 200 that includes the ophthalmoscope 100. The electrical signal is processed by a control unit 212 into an image of the eye 111, and the image is displayed on a display 216.

The wavefront sensor 115 is connected to the control unit 212. The received wavefront is transferred to the control unit 212. The wavefront correction device 108 is also connected to the control unit 212 and performs modulation as instructed by the control unit 212. The control unit 212 calculates a modulation amount (correction amount) for correction of the wavefront based on the wavefront obtained by a measuring result of the wavefront sensor 115, and instructs the wavefront correction device 108 to perform the modulation according to the modulation amount. The wavefront measurement and the instruction to the wavefront correction device 108 are repeated and feedback control is performed so as to obtain a suitable wavefront.

In an exemplary embodiment the light division portion 104 is a fused fiber coupler. In an alternative exemplary embodiment, the light division portions 104 and 106 include partially reflective mirrors.

The detector 114 may detect reflections or fluorescence associated with the scanning spot. The detection system may make use confocal microscopy techniques in which an aperture associated with the scanning spot is used to increase the resolution and/or contrast of the detection system. The system may also include a reference arm and the detector 114 may be part of a detection system used to detect an interference signal.

The wavefront sensor 115, the wavefront correction device 108, and the scanners 109 may all be positioned at a first set of conjugate planes that are all optically conjugate with each other. Positioned at the conjugate planes, in the context of the present application, means substantially close to an ideal conjugate planes within normal alignment tolerances. Both of the first scanner 109-1 and the second scanner 109-2 may also be positioned at planes which belong to the first set of conjugate planes. The first set of conjugate planes may also be conjugate pupil planes. The first set of conjugate planes may also include a system pupil plane 110 which is conjugate with all of the other conjugate planes. The system pupil plane 110 may be located at or near the eye 111.

The ophthalmoscope 100 need a focusing means in addition to the wavefront correction device 108 in order to achieve a high dioptric range (for example, ±10 Diopters (D)) since the maximum stroke of the wavefront correction device 108 is not sufficient to correct high defocus associated with typical range of exam patients. It is not difficult to implement the focusing means with lenses but eccentric mirror optics are typically used in Adaptive Optic systems to avoid back-reflection light from the lens surface incident to a wavefront sensor 115.

Figure 3:
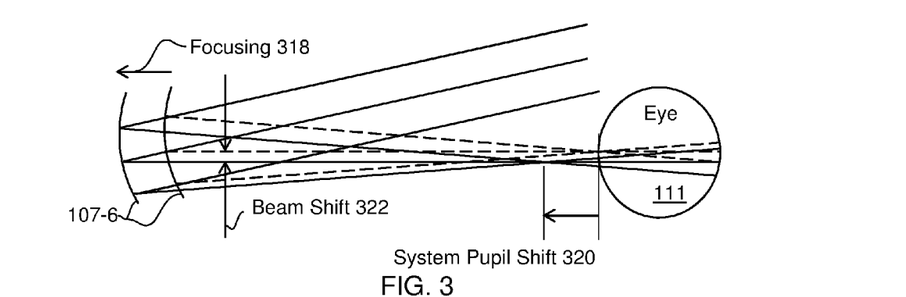
FIG. 3 is an illustration of a focusing method used in an ophthalmoscope.

FIG. 3 is an illustration of a first focusing method that may be used in an ophthalmoscope 300 substantially similar to ophthalmoscope 100. The focus may be adjusted by moving mirror 107-6 away or toward the eye 111 as illustrated by arrow 318 this has an effect of moving the system pupil plane 110 as illustrated in FIG. 3 along arrow 320. Using this method to focus has the disadvantage of also shifting the beam while changing the focus of the beam as shown by arrows 322. This has an effect on the wavefront correction performance.

Figure 4:
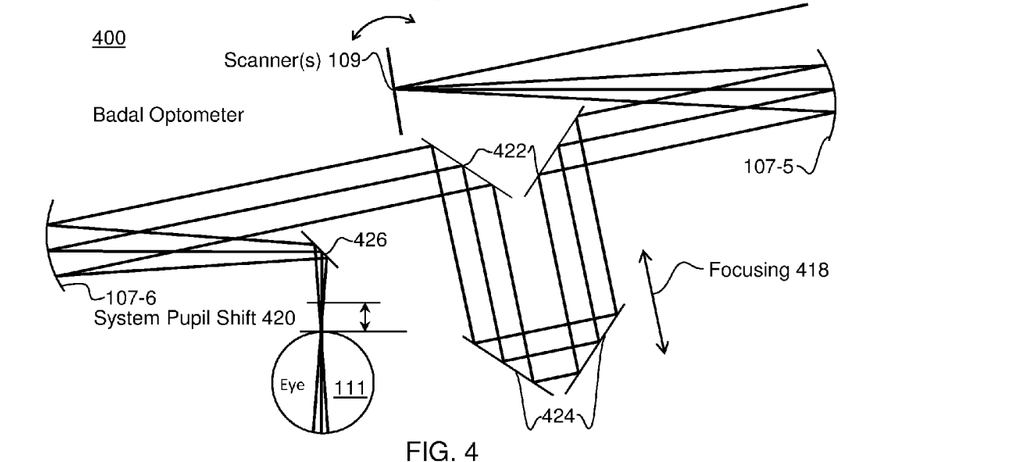
FIG. 4 is an illustration of Badal ophthalmoscope.

FIG. 4 is an illustration of a Badal optometer 400 that includes folding mirrors that can be used to adjust the focus of the optometer 400. The Badal optometer 400 may be substantially similar to the optometer 100 and include at least scanner(s) 109 and mirrors 107-5 and 107-6. The Badal optometer 400 may also include folding mirrors 422 between mirrors 107-5 and 107-6. The Badal optometer 400 may also include focusing mirrors 424 between folding mirrors 422. The focusing mirrors 424 may be moved along arrow 418 by a translation stage to shift the system pupil plane 110 as illustrated by arrow 420. A turning mirror 426 may direct the light into the eye 111. The focal point of the Badal Optometer may adjusted without causing the beam shift introduced by the focusing method of translating mirror 107-6. The Badal optometer 400 has trouble achieving high dioptric range. Because each concave mirror has to have long focal length to avoid mechanical interference and beam clipping and to minimize the system aberration generated by the decentered spherical mirrors but the system does not have enough optical power to correct large defocus even if the optometer has large translation stroke.

Figure 5A:
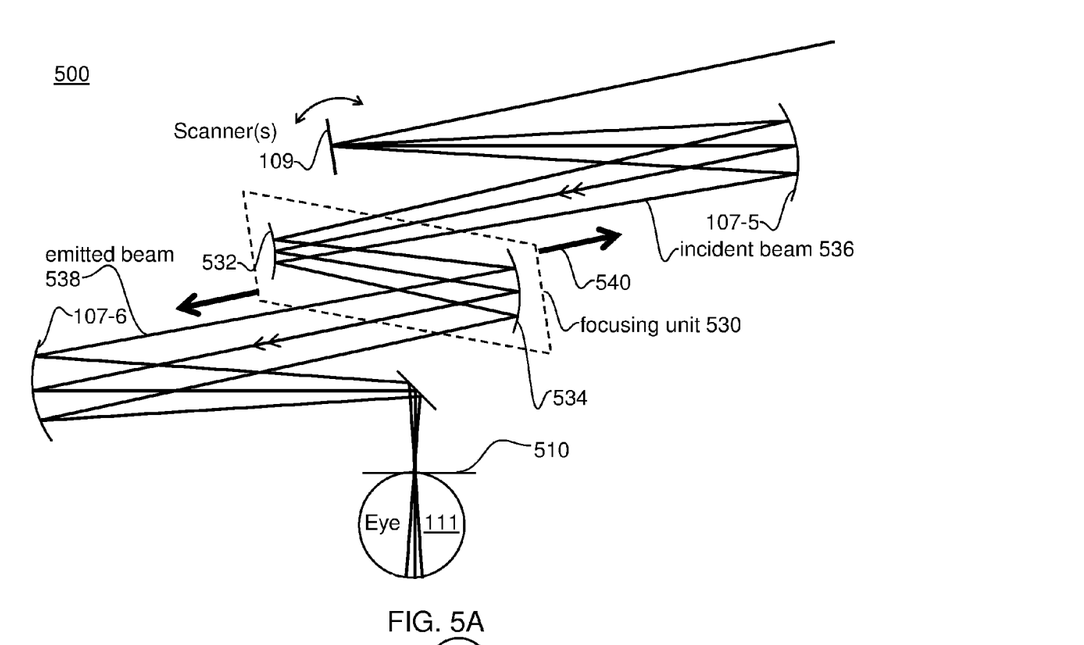
FIG. 5A is an illustration of a portion of an ophthalmoscope using a focusing method according to an embodiment.

FIG. 5A is an illustration of a focusing method that may be used in an ophthalmoscope 500 substantially similar to ophthalmoscope 100. The ophthalmoscope 500 has all of the components of ophthalmoscope 100 and also includes a focusing unit translation stage 530. A first focusing mirror 532 and a second focusing mirror 534 are mounted on the focus translation stage 530. The focusing unit translation stage 530 fixes the relative position of the first focusing mirror 532 and the second focusing mirror 534. The focus translation stage may be moved by linear motor, screw motors, piezoelectric motors, electromagnetic motors, capacitive motors, induction motors, step motors, push-pull motors, mems motors, and any other motor which can translate the focus translation stage while maintaining the optical alignment. In one embodiment, an incident beam 536 of light enters the focusing unit is reflected off the first focusing mirror 532 onto the second focusing mirror 534 and exits the focusing unit as an emitted beam 538 of light. The first focusing mirror 532 and the second focusing mirror 534 are arranged such that an optical axis of the incident beam 536 and an optical axis of the emitted beam 538 are substantially parallel to each other. The optical power and position of the first focusing mirror 532 and the second focusing mirror 534 are each arranged such that the exit pupil at the system pupil plane 510 stays at the same axial position when the focusing unit moves. In one embodiment, the incident beam 536 is not collimated when it strikes the first focusing mirror 532, the incident beam may be collimated before it strikes mirror 107-5. In one embodiment, the first focusing mirror 532 is a convex mirror. In one embodiment, the second focusing mirror 534 is a concave mirror.

Figure 5B:
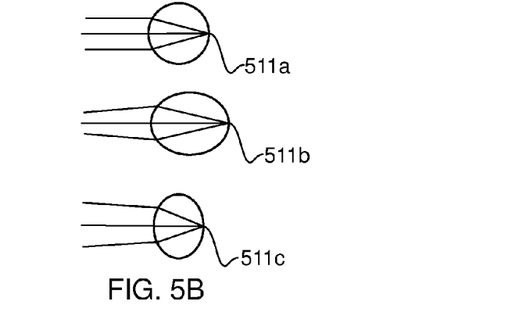
FIG. 5B is an illustration of different types of eyes.

The focus translation stage 530 moves along a translation axis 540 that is substantially parallel to the optical axis of the incident beam 536 and the optical axis of the emitted beam 538. Moving the translation stage along the translation axis 540 shifts the focus of the optical system. While the focus is changed by moving the translation stage the plurality of optically conjugate planes include system pupil do not substantially move. In the context of the present application, not substantially moving means it is within alignment and/or stability tolerances which are determined by the imaging accuracy of the ophthalmoscope. This shift in focus can be used to compensate for defocus generated by the subject being examined. For example, FIG. 5B is an example of three eyes: an eye 511a in a state of emmetropia, perfect vision requiring no correction; an eye 511b in a state of myopia; and an eye 511c in a state of hyperopia. When the subject has an eye 511a, the focus translation stage 530 may be located at central neutral position. When the subject has an eye 511b, the focus translation stage 530 may be translated along the translation axis 540 towards mirror 107-5 to compensate for the myopia in the subjects eye. When the subject has an eye 511c, the focus translation stage 530 may be translated along the translation axis 540 towards mirror 107-6 to compensate for hyperopia in the subject's eye.

In one embodiment the defocus is generated solely by the subject 111. In another embodiment, some of the defocus may be inherent within the ophthalmoscope 500, and may vary over time. The defocus may be detected by a dedicated defocus sensor that is included in the detector 114. The defocus may also be detected by analyzing an image generated with the detector 114. The wavefront sensor 115 may also be used to detect the defocus. A combination of two or more of a dedicated defocus sensor, image analysis using an image generated with the detector, and the wavefront sensor may be used to detect the defocus.

In one embodiment, wavefront correction is performed after the defocus is corrected, thus providing the ophthalmoscope 500 with stable and predictable results. In another embodiment, the wavefront correction and the defocus may also be performed at the same time, thus providing the ophthalmoscope 500 with a faster measurement time. In another embodiment, the wavefront correction may be started when the defocus amount is below a threshold but while the focusing unit continues to adjust the focus, thus providing a compromise that is both stable and fast.

Figure 6A:
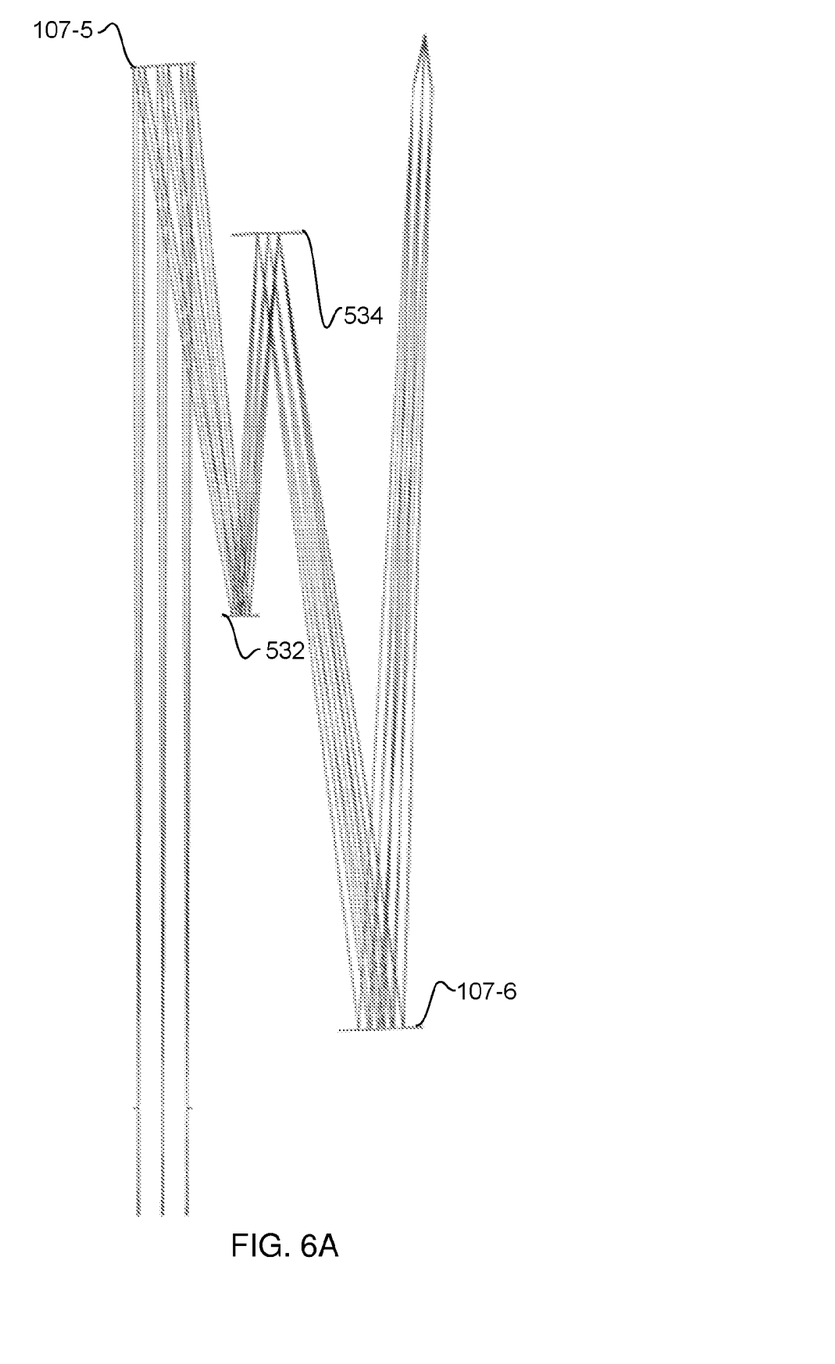
FIGS. 6A-C are illustrations of ray traces of an ophthalmoscope at different focus points.
Figure 6B:
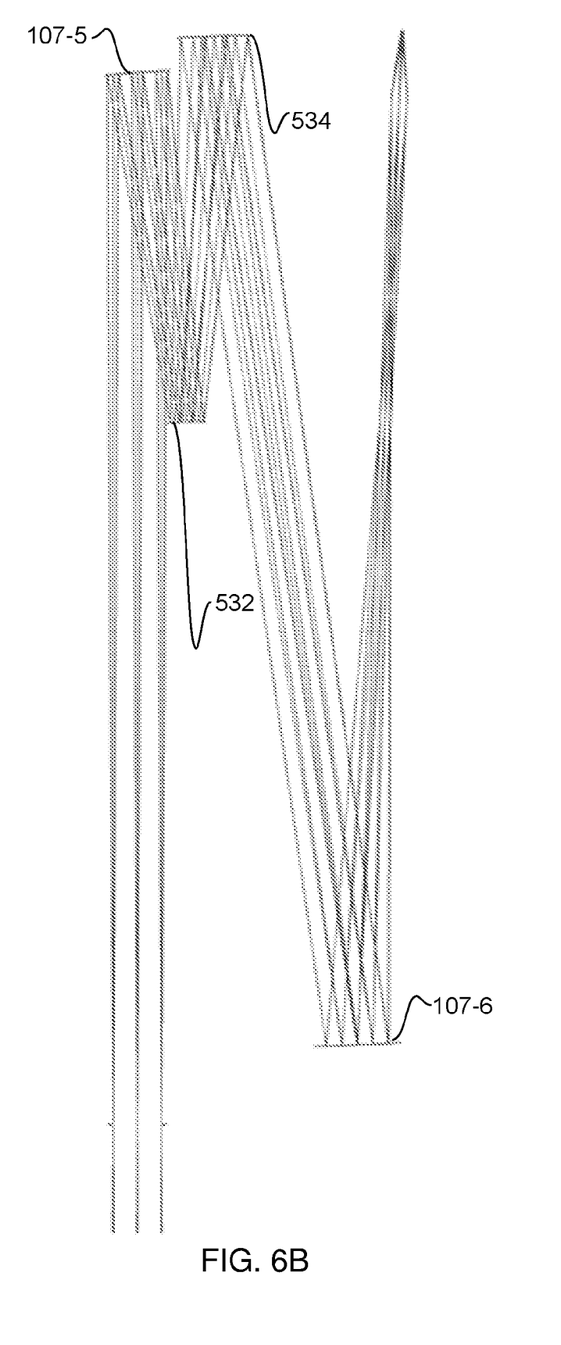
Figure 6C:
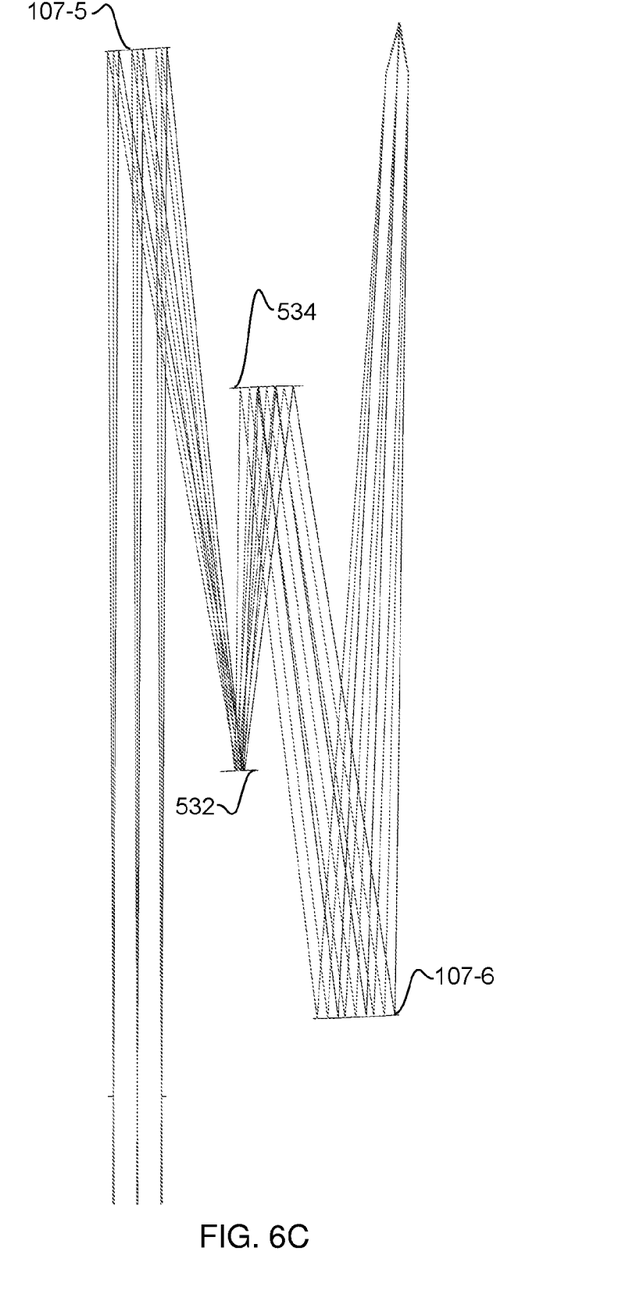
Figure 7A:
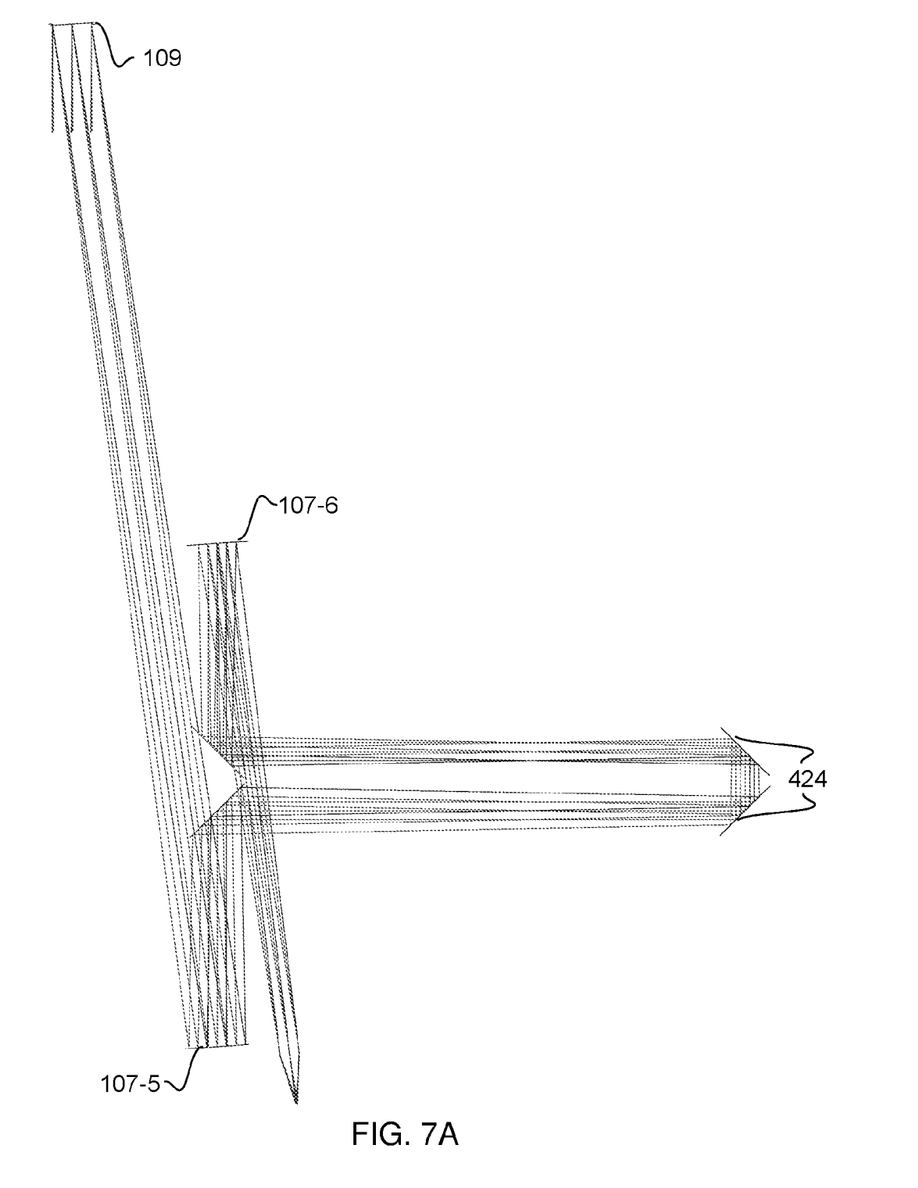
FIGS. 7A-C are illustrations ray traces of a Badal Optometer at different focus points.
Figure 7B:
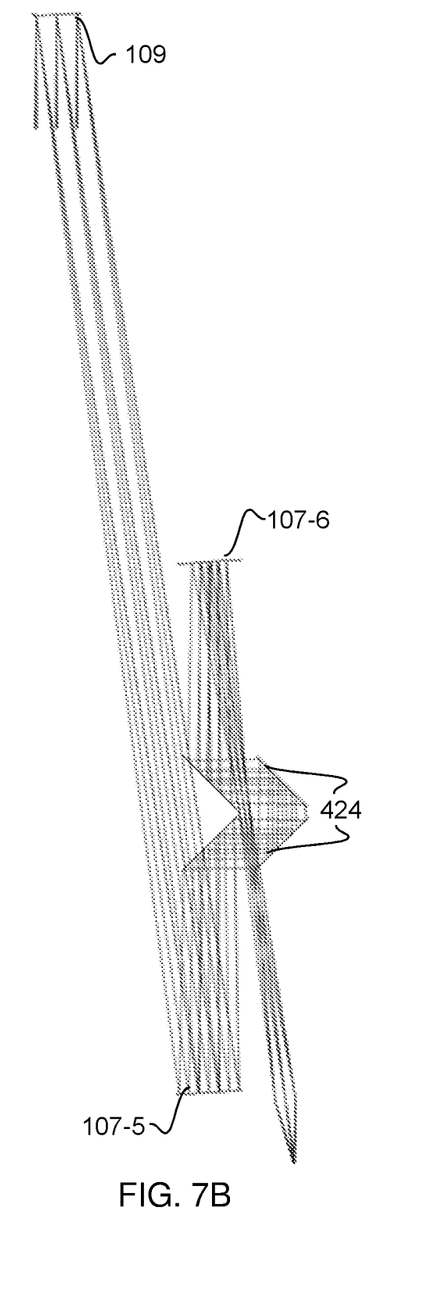
Figure 7C:
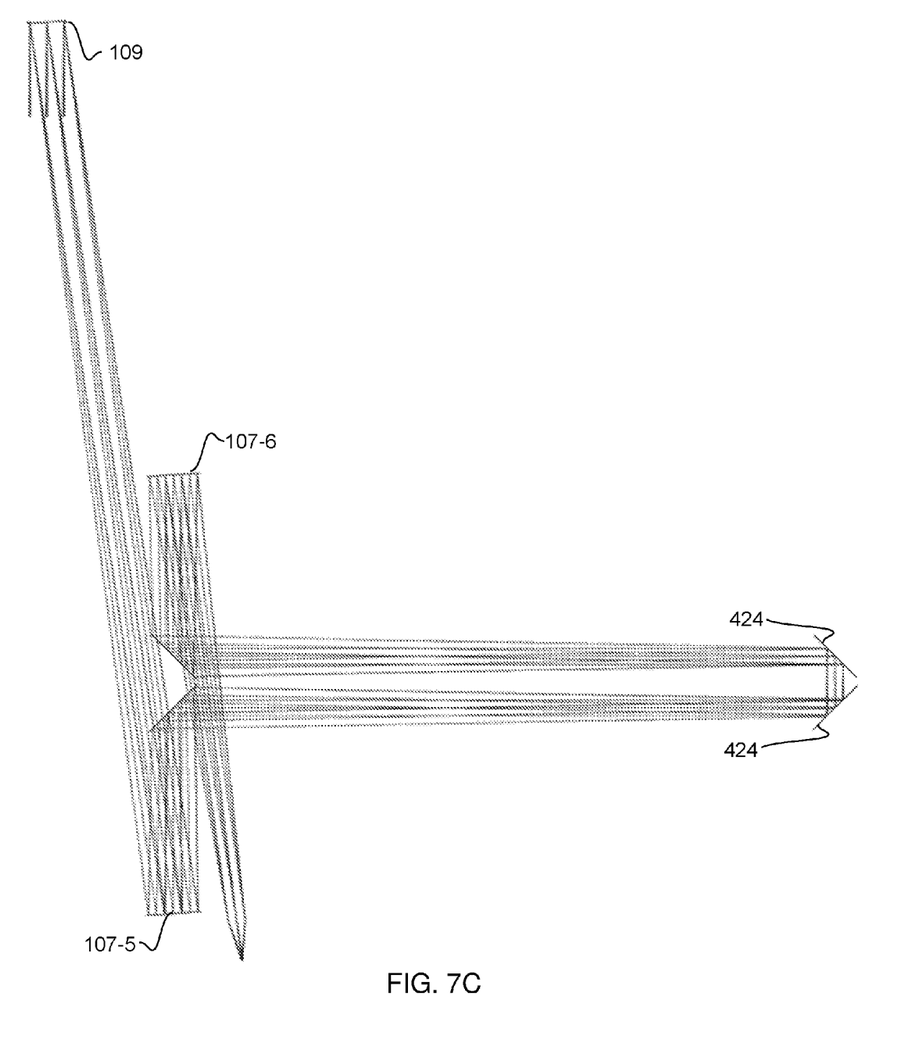
Figure 8A:
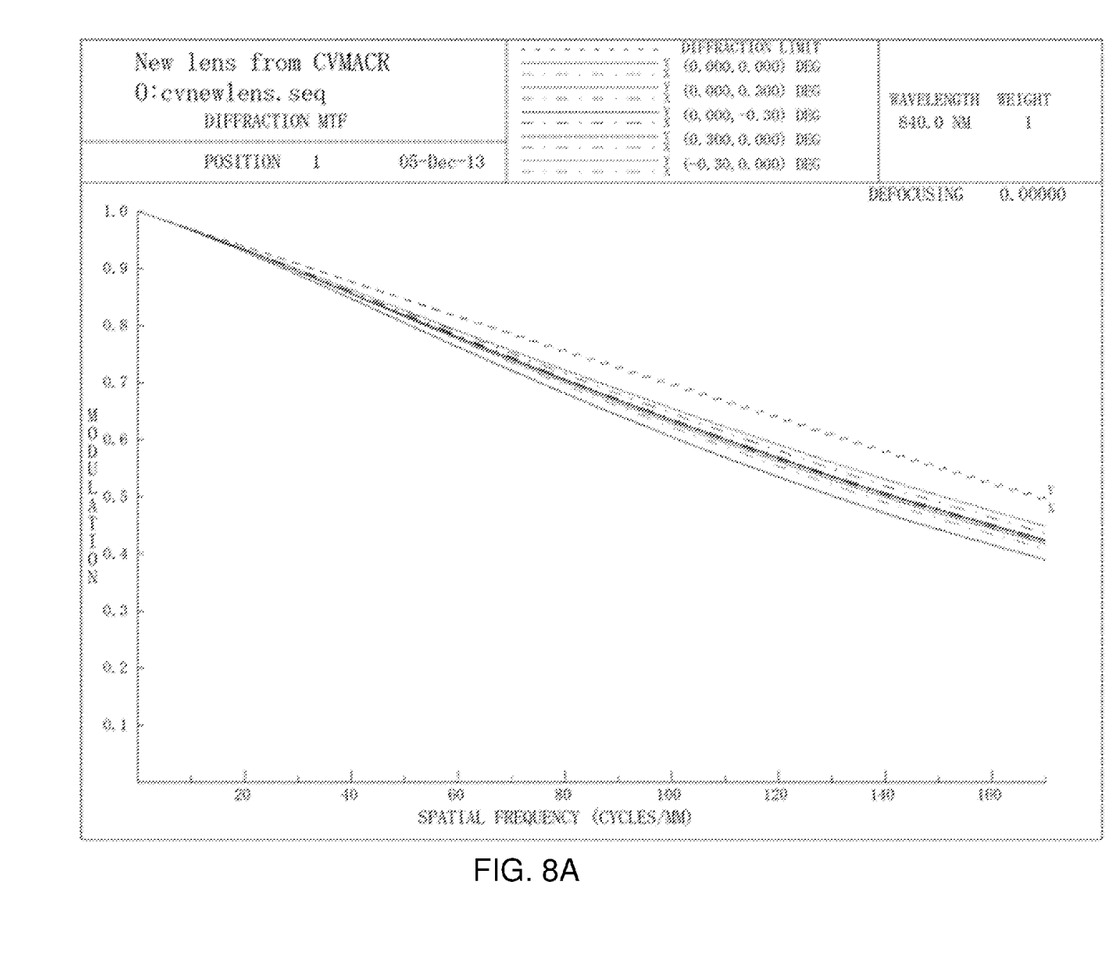
FIGS. 8A-C are illustrations of the optical performance of an ophthalmoscope.
Figure 8B:
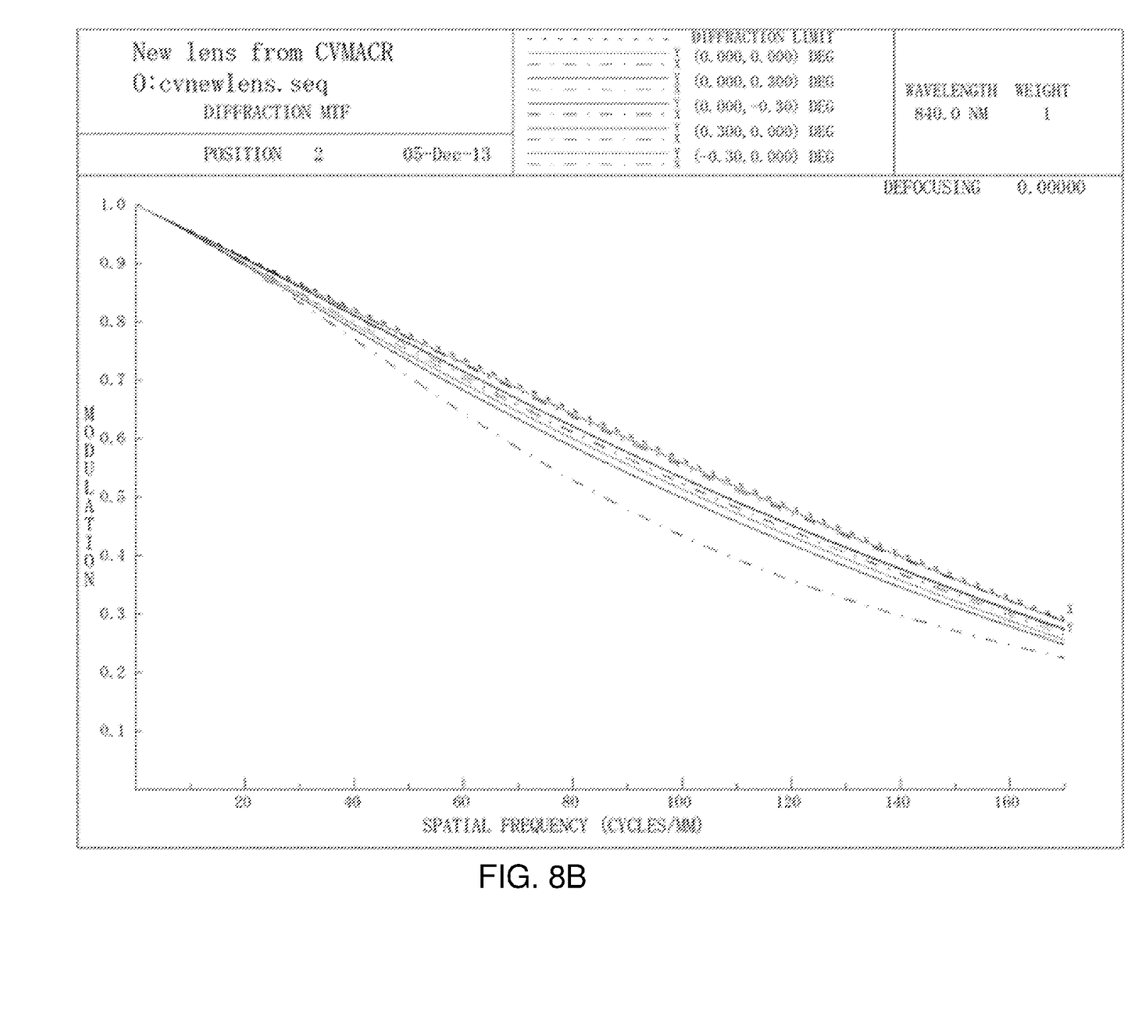
Figure 8C:
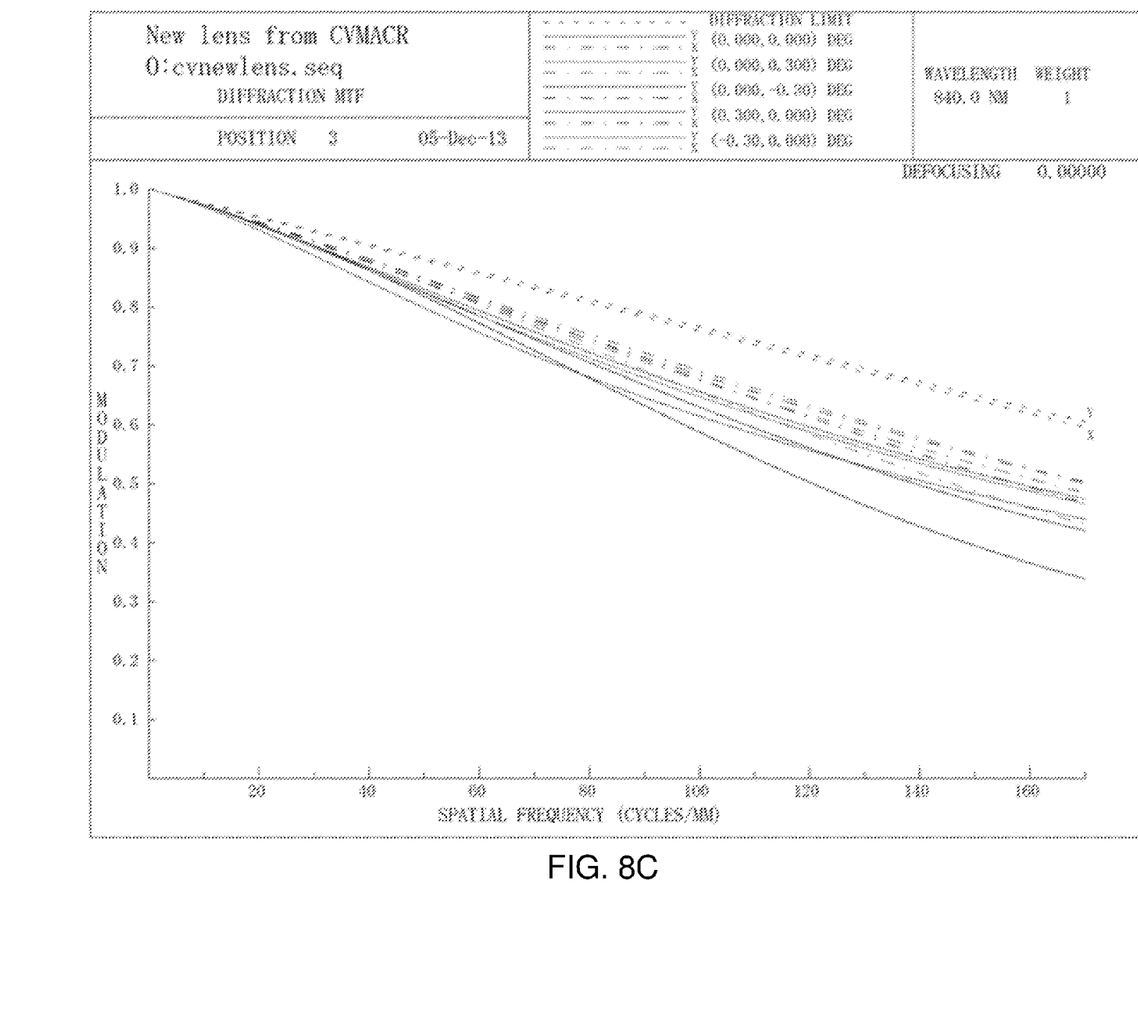

FIGS. 6A-C are illustrations of ray traces of the ophthalmoscope 500 at different focus points. FIGS. 7A-C are illustrations ray traces of a Badal Optometer 400 at different focus points. FIG. 8AC are illustrations of the performance of the ophthalmoscope 500 at three different positions of the focusing unit 530, in which the modulation transfer function is illustrated relative to diffraction limit.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An apparatus for measuring a fundus of a subject comprising:
   a scanner configured to scan light from a light source on the fundus of the subject; and
   a focusing unit which adjusts a defocus comprising:
      a first focusing mirror;
      a second focusing mirror;
      a first focusing optical member; and
      a second focusing optical member,
      wherein a first optical path between the first focusing optical member and the first focusing mirror and a second optical path between the second focusing mirror and the second focusing optical member are substantially parallel to each other,
      wherein the focusing unit is positioned between the scanner and the subject,
      wherein adjustment of the defocus is accomplished by changing a length of the first optical path and a length of the second optical path by moving both the first focusing mirror and the second focusing mirror substantially parallel to the first optical path and the second optical path, and
      wherein an optical path length between the scanner and the subject does not substantially change as the defocus is adjusted by moving both the first focusing mirror and the second focusing mirror.

2. The apparatus according to claim 1, further comprising the light source.

3. The apparatus according to claim 1, wherein one of the first focusing mirror and the second focusing mirror is a concave mirror and the other is a convex mirror.

4. The apparatus according to claim 1, wherein the relative position of the first focusing mirror to the second focusing mirror remains unchanged during focusing.

5. The apparatus according to claim 1, wherein a plurality of optically conjugate planes does not move during focusing.

6. The apparatus according to claim 1, wherein the defocus is generated by the subject.

7. The apparatus according to claim 1, wherein a beam from the first focusing optical member is not collimated when the beam strikes the first focusing mirror.

8. The apparatus according to claim 1, further comprising;
a wavefront sensor configured to detect a shape of a wavefront; and
a wavefront correction device;
wherein the wavefront correction device adjusts a wavefront of the light from the light source based on the shape of the wavefront detected by the wavefront sensor, and is positioned between the focusing unit and the light source, and
wherein an optical lens is not arranged on an optical path between the wavefront correction device and the subject.

9. The apparatus according to claim 8, wherein:
the wavefront sensor detects the defocus generated by the subject, and
the focusing unit corrects the defocus by moving the first focusing mirror and the second focusing mirror based on the defocus detected by the wavefront sensor.

10. The apparatus according to claim 8, further comprising a detector for detecting light from the fundus of the subject which has been reflected by the first and second focusing mirrors and has been corrected by the wavefront correction device.

11. The apparatus according to claim 8, wherein the scanner is positioned between the wavefront correction device and the focusing unit.

12. The apparatus according to claim 8 wherein:
the wavefront sensor is positioned at a first conjugate plane;
the wavefront correction device is positioned at a second conjugate plane, and wherein the first conjugate plane and the second conjugate plane are substantially optically conjugate with each other.

13. The apparatus of claim 12 further comprising a detector for detecting light from the fundus of the subject, the detector being positioned at a third conjugate plane;
wherein the scanner is positioned at a fourth conjugate plane, and
wherein the first, the second, the third, and the fourth conjugate planes are substantially optically conjugate with each other.

14. The apparatus according to claim 8, wherein the wavefront correction device corrects aberrations while the focusing unit is correcting defocus.

15. The apparatus according to claim 14, wherein the wavefront correction device starts correcting aberrations after the focusing unit has started correcting defocus and a defocus amount is below a threshold, and the focusing unit continues to adjust defocus.

16. An ophthalmic apparatus for measuring a fundus of a subject comprising:
a scanner for scanning light from a light source on the fundus of the subject;
a focusing unit which adjusts a defocus comprising:
a first focusing mirror;
a second focusing mirror;
a first focusing optical member; and
a second focusing optical member,
wherein a first optical path between the first focusing optical member and the first focusing mirror and a second optical path between the second focusing mirror and the second focusing optical member are substantially parallel to each other,
wherein the focusing unit is positioned between the scanner and the subject,
wherein adjustment of the defocus is accomplished by changing a length of the first optical path and a length of the second optical path by moving both the first focusing mirror and the second focusing mirror substantially parallel to the first optical path and the second optical path, and
wherein an optical path length between the scanner and the subject does not substantially change as the defocus is adjusted by moving both the first focusing mirror and the second focusing mirror;
a wavefront sensor for detecting a shape of a wavefront; and
a wavefront correction device;
wherein the wavefront correction device adjusts a wavefront of the light from the light source based on the shape of the wavefront detected by the wavefront sensor, and is positioned between the focusing unit and the light source, and
wherein an optical path length between the scanner and the subject does not substantially change as the defocus is adjusted by moving both the first focusing mirror and the second focusing mirror.

17. The apparatus according to claim 16, wherein one of the first focusing mirror and the second focusing mirror is a concave mirror and the other is a convex mirror.

18. The apparatus according to claim 16, wherein the ophthalmic apparatus is an adaptive optics scanning light ophthalmoscope.

19. The apparatus according to claim 17, wherein the ophthalmic apparatus is an adaptive optics optical coherence tomographic apparatus.

* * * * *